US010684691B2

(12) United States Patent
Hayashi et al.

(10) Patent No.: US 10,684,691 B2
(45) Date of Patent: Jun. 16, 2020

(54) GESTURE DETECTION SUPPORTING SYSTEM FOR X-RAY DIAGNOSIS

(71) Applicant: TOSHIBA MEDICAL SYSTEMS CORPORATION, Otawara-Shi (JP)

(72) Inventors: Yoshiyasu Hayashi, Nasushiobara (JP); Yuichiro Watanabe, Yaita (JP); Jun Sakakibara, Otawara (JP); Ko Fuchigami, Otawara (JP); Yusuke Kanno, Otawara (JP); Masaki Akiyama, Otawara (JP)

(73) Assignee: Canon Medical Systems Corporation, Otawara-shi (JP)

(*) Notice: Subject to any disclaimer, the term of this patent is extended or adjusted under 35 U.S.C. 154(b) by 294 days.

(21) Appl. No.: 14/717,380

(22) Filed: May 20, 2015

(65) Prior Publication Data
US 2015/0253865 A1 Sep. 10, 2015

Related U.S. Application Data

(63) Continuation of application No. PCT/JP2013/081519, filed on Nov. 22, 2013.

(30) Foreign Application Priority Data

Nov. 25, 2012 (JP) .................. 2012-256994

(51) Int. Cl.
G06F 3/01 (2006.01)
A61B 6/00 (2006.01)
G06F 3/03 (2006.01)

(52) U.S. Cl.
CPC .............. G06F 3/017 (2013.01); A61B 6/467 (2013.01); A61B 6/481 (2013.01); A61B 6/54 (2013.01); G06F 3/0304 (2013.01)

(58) Field of Classification Search
CPC ...................................................... G06F 3/017
See application file for complete search history.

(56) References Cited

U.S. PATENT DOCUMENTS 6,175,610 B1 1/2001 Peter
7,835,498 B2 11/2010 Bonfiglio et al.
(Continued)

FOREIGN PATENT DOCUMENTS

CN 101119680 A 2/2008
JP 11-313801 A 11/1999
(Continued)

OTHER PUBLICATIONS

Combined Chinese Office Action and Search Report dated Sep. 22, 2015 in Patent Application No. 201380003004.9 (with English Translation of Category of Cited Documents).
(Continued)

Primary Examiner — Rochelle D Turchen
(74) Attorney, Agent, or Firm — Oblon, McClelland, Maier & Neustadt, L.L.P.

(57) ABSTRACT

According to one embodiment, a gesture detection supporting system for an X-ray diagnosis includes memory circuitry, a sensor, processing circuitry and an attaching instrument. The memory circuitry stores an operation content of an X-ray diagnostic apparatus. The operation content is related to a gesture by a user. The sensor senses a gesture. The processing circuitry detects the gesture, based on an output from the sensor; acquire the operation content of the X-ray diagnostic apparatus, from the memory circuitry, based on a detection result of the gesture; and output operation information to the X-ray diagnostic apparatus, based on the operation content. The attaching instrument attaches the sensor to a ceiling of an examination room, an arm for driving an X-ray tube and an X-ray detector, an intravenous drip stand, an injector of a contrast agent, an
(Continued)

X-ray protective board and/or a display for displaying an X-ray image.

11 Claims, 8 Drawing Sheets

(56) References Cited

U.S. PATENT DOCUMENTS

| | | |
|---|---|---|
| 9,159,151 B2 | 10/2015 | Perez et al. |
| 2011/0026678 A1 | 2/2011 | Bonfiglio et al. |
| 2011/0060423 A1 | 3/2011 | Bonfiglio et al. |
| 2012/0249977 A1* | 10/2012 | Abri ................ G03B 21/00 353/69 |
| 2013/0050425 A1* | 2/2013 | Im .................... G06F 3/005 348/46 |

FOREIGN PATENT DOCUMENTS

| | | |
|---|---|---|
| JP | 2008-529707 A | 8/2008 |
| JP | 2012-058854 A | 3/2012 |
| JP | 2012-070862 A | 4/2012 |
| JP | 2012-533134 A | 12/2013 |

OTHER PUBLICATIONS

Japanese Office Action dated Sep. 13, 2016 in Patent Application No. 2012-256994.
Office Action dated May 2, 2017 in Japanese Patent Application No. 2012-256994.
International Preliminary Report on Patentability and Written Opinion dated Jun. 4, 2015 in PCT/JP2013/081519 (English translation only).
International Search Report dated Jan. 14, 2014 in PCT/JP2013/081519 filed Nov. 22, 2013.

* cited by examiner (A) GESTURE OPERATION OFF (B) GESTURE OPERATION ON (A) GESTURE OPERATION OFF (B) GESTURE OPERATION ON

GESTURE DETECTION SUPPORTING SYSTEM FOR X-RAY DIAGNOSIS

CROSS REFERENCES TO RELATED APPLICATIONS

This is a continuation of Application PCT/JP2013/81519, filed on Nov. 22, 2013.

This application is based upon and claims the benefit of priority from Japanese Patent Application No. 2012-256994, filed on Nov. 25, 2012; the entire contents of which are incorporated herein by reference.

FIELD

Embodiments described herein relate generally to a gesture detection supporting system for an X-ray diagnosis, an X-ray diagnostic apparatus and a gesture detection supporting method.

BACKGROUND

Conventionally, gesture detection technology using a depth sensor and an optical camera is known. Furthermore, technology for controlling a game machine by gestures is also known as an application of the gesture detection technology. Accordingly, technology using gestures in order to operate an X-ray diagnostic apparatus is proposed.

However, an examination room where an X-ray diagnostic apparatus is installed and operators of an X-ray diagnostic apparatus during an operation have various restrictions. For example, various medical devices are installed in an examination room. For this reason, a field of view of a detector, such as a depth sensor and an optical camera, may be interrupted by medical devices, depending on a placed position of the detector. Moreover, it is desired to decrease actions and ranges of actions to operate an X-ray diagnostic apparatus as much as possible so that an operator can fully concentrate a procedure.

Thus, X-ray diagnoses have particular restrictions. For this reason, operation functions of an X-ray diagnostic apparatus by gestures cannot be used effectively in some cases.

Accordingly, an object of the present invention is to provide a gesture detection supporting system for an X-ray diagnosis, an X-ray diagnostic apparatus, and a gesture detection supporting method which make it possible to effectively utilize an operation function of the X-ray diagnostic apparatus by gestures under restrictions peculiar to an X-ray diagnosis.

DETAILED DESCRIPTION

Figure 1:
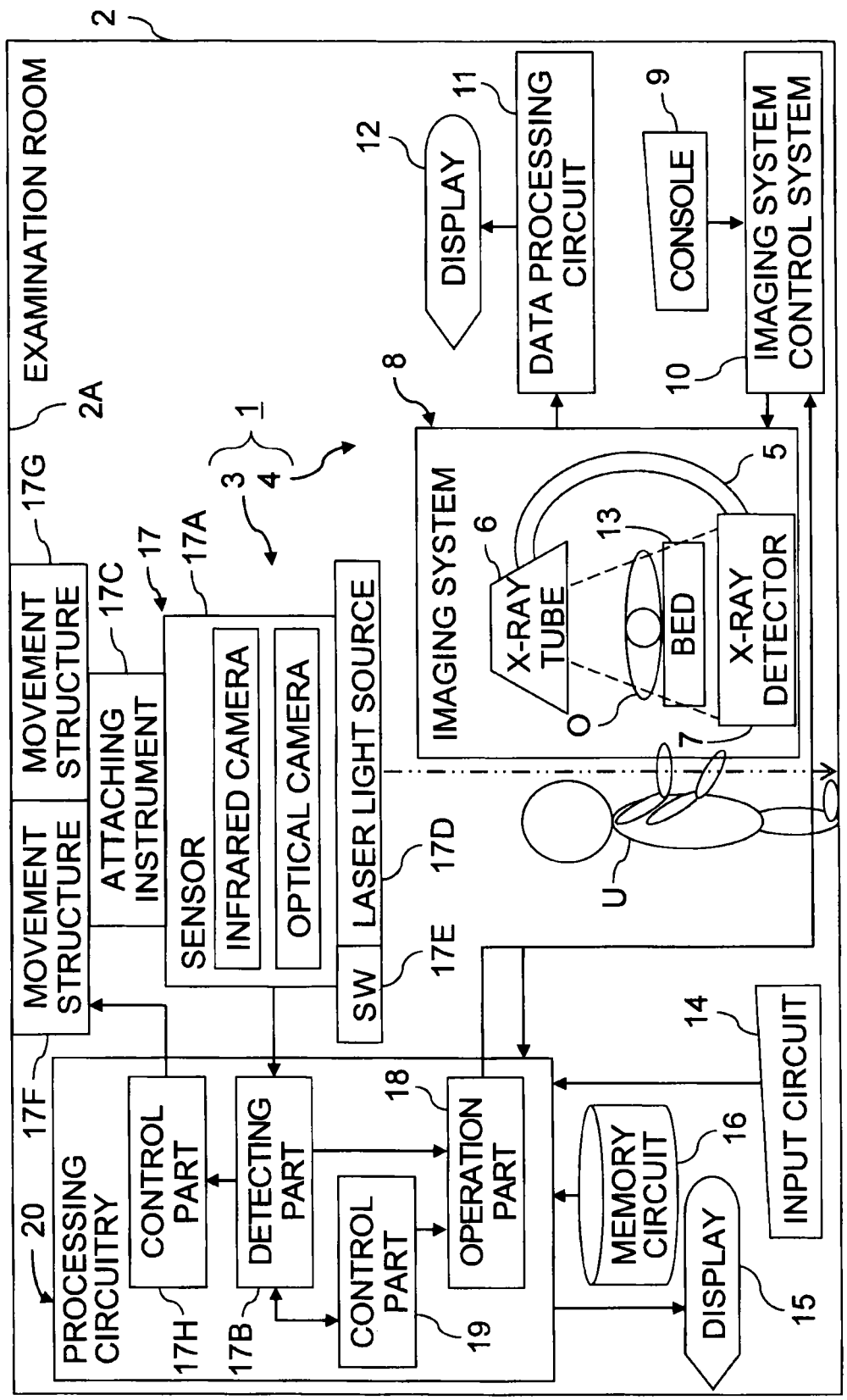
FIG. 1 is a functional block diagram showing a configuration of an X-ray diagnostic apparatus having a gesture detection supporting system for an X-ray diagnosis according to an embodiment of the present invention.

In general, according to one embodiment, a gesture detection supporting system for an X-ray diagnosis includes memory circuitry, at least one sensor, processing circuitry and an attaching instrument. The memory circuitry is configured to store an operation content of an X-ray diagnostic apparatus. The operation content is related to a gesture by an assumed user. The at least one sensor is configured to sense a gesture by an actual user. The processing circuitry is configured to detect the gesture by the actual user, based on an output from the at least one sensor; acquire the operation content of the X-ray diagnostic apparatus, from the memory circuitry, based on a detection result of the gesture by the actual user; and output operation information to the X-ray diagnostic apparatus, based on the acquired operation content. The attaching instrument is configured to attach the at least one sensor to at least one of a ceiling of an examination room in which the X-ray diagnostic apparatus is placed, an arm for driving an X-ray tube and an X-ray detector of the X-ray diagnostic apparatus, an intravenous drip stand, an injector of a contrast agent, an X-ray protective board and a display for displaying an X-ray image acquired by the X-ray diagnostic apparatus.

Further, according to another embodiment, a gesture detection supporting system for an X-ray diagnosis includes memory circuitry and processing circuitry. The memory circuitry is configured to store an operation content of an X-ray diagnostic apparatus. The operation content is related to a gesture by an assumed user. The processing circuitry is configured to detect a gesture by an actual user, based on an output from a sensor; acquire the operation content of the X-ray diagnostic apparatus, from the memory circuitry, based on a detecting result of the gesture by the actual user; output operation information to the X-ray diagnostic apparatus, based on the acquired operation content; detect at least one of a relative position relationship between a wrist and an elbow of the actual user and a catheter, based on another output from the sensor or another sensor; and stop at least one of detecting a following gesture by the actual user and outputting following operation information when the relative position relationship between the wrist and the elbow has become a predetermined condition or when the catheter is determined to be held with a hand of the actual user.

Further, according to another embodiment, a gesture detection supporting system for an X-ray diagnosis includes memory circuitry and processing circuitry. The memory circuitry is configured to store an operation content of an X-ray diagnostic apparatus. The operation content is related to a gesture by only a forearm of an assumed user or a gesture by a part, including a shoulder and a wrist and excluding an elbow, of the assumed user. The processing circuitry is configured to detect a gesture by only a forearm of an actual user or a gesture by a part, including a shoulder and a wrist and excluding an elbow, of the actual user, based on an output from a sensor; acquire the operation content of the X-ray diagnostic apparatus, from the memory circuitry, based on a detection result of the gesture by the actual user; and output operation information to the X-ray diagnostic apparatus, based on the acquired operation content.

Further, according to another embodiment, a gesture detection supporting system for an X-ray diagnosis includes memory circuitry and processing circuitry. The memory circuitry is configured to store an operation content of an X-ray diagnostic apparatus. The operation content is related to a gesture by an assumed user. The processing circuitry is configured to specify an actual user from candidates, based on an output from a sensor; detect a gesture by the specified actual user, based on another output from the sensor or another sensor; acquire the operation content of the X-ray diagnostic apparatus, from the memory circuitry, based on a detection result of the gesture by the actual user; and output operation information to the X-ray diagnostic apparatus, based on the acquired operation content.

Further, according to another embodiment, an X-ray diagnostic apparatus includes the above mentioned gesture detection supporting system for the X-ray diagnosis, the X-ray tube and the X-ray detector. The X-ray tube and the X-ray detector are configured to perform X-ray imaging according to the operation information.

Further, according to another embodiment, a gesture detection supporting method includes: storing an operation content, related to a gesture by an assumed user, of an X-ray diagnostic apparatus; sensing a gesture by an actual user, with at least one sensor; detecting the gesture by the actual user, based on an output from the at least one sensor; acquiring the operation content of the X-ray diagnostic apparatus, from the memory circuitry, based on a detection result of the gesture by the actual user; outputting operation information to the X-ray diagnostic apparatus, based on the acquired operation content; and attaching the at least one sensor, by an attaching instrument, to at least one of a ceiling of an examination room in which the X-ray diagnostic apparatus is placed, an arm for driving an X-ray tube and an X-ray detector of the X-ray diagnostic apparatus, an intravenous drip stand, an injector of a contrast agent, an X-ray protective board and a display for displaying an X-ray image acquired by the X-ray diagnostic apparatus.

A gesture detection supporting system for an X-ray diagnosis, an X-ray diagnostic apparatus and a gesture detection supporting method according to embodiments of the present invention will be described with reference to the accompanying drawings.

FIG. 1 is a functional block diagram showing a configuration of an X-ray diagnostic apparatus having a gesture detection supporting system for an X-ray diagnosis according to an embodiment of the present invention.

An X-ray diagnostic apparatus 1 is installed in an examination room 2. Furthermore, a gesture detection supporting system 3 is installed, as an appendage system of the X-ray diagnostic apparatus 1 or a system independent from the X-ray diagnostic apparatus 1, in an examination room 2. In the example shown in FIG. 1, the X-ray diagnostic apparatus 1 includes an X-ray image acquisition system 4 and the gesture detection supporting system 3. Note that, FIG. 1 shows functions mainly, and an arrangement of each instrument shown in FIG. 1 does not necessarily accord with an actual arrangement.

The X-ray image acquisition system 4 composes the main part, of the X-ray diagnostic apparatus 1, for acquiring X-ray diagnostic image data of an object O by exposing an X-ray to the object O. Specifically, the X-ray image acquisition system 4 includes an imaging system 8, a console 9, an imaging system control circuit 10, a data processing circuit 11, a display 12 and a bed 13 for setting an object O. The imaging system 8 is configured by providing at the both ends of an arm 5 with an X-ray tube 6 and an X-ray detector 7. The console 9 can be configured by a display and an input circuit such as a mouse, a keyboard, a trackball, a touch panel and a touch pad. The imaging system control system 10 is configured to output control information to the imaging system 8 according to operation information of the console 9. Specifically, the imaging system control system 10 includes a high voltage generator for applying a voltage with the X-ray tube 6, an arm driving structure for driving the arm 5, a bed driving structure for driving the bed 13 and processing circuitry for controlling them. The data processing circuit 11 is configured to generate X-ray image data based on X-ray detection data acquired by the imaging system 8. The display 12 is configured to display X-ray image data.

The processing circuitry of the imaging system control system 10 and the data processing circuit 11 can be configured by a single circuit or plural circuits. For example, they may be at least one CPU (central processing unit), at least one GPU (graphics processing unit), at least one ASIC (application specific integrated circuit), and/or at least one PLD (programmable logic device), such as an SPLD (simple PLD), a CPLD (complex PLD) and an FPGA (field programmable gate array). Then, they read program from a memory circuitry and execute the read program.

The gesture detection supporting system 3 is configured to detect gestures of a user U in order to operate the X-ray diagnostic apparatus 1 by the gestures. Therefore, the X-ray image acquisition system 4 of the X-ray diagnostic apparatus 1 is configured to perform X-ray imaging according to operation information from the gesture detection supporting system 3. On the other hand, the gesture detection supporting system 3 has an input circuit 14, a display 15, memory circuitry 16, a detecting system 17, an operation part 18, and a control part 19. Examples of the input circuit 14 include a mouse, a keyboard, a trackball, a touch panel and a touch pad.

The elements for executing processing of digital information among the elements of the gesture detection supporting system 3 can be made by processing circuitry 20 reading a gesture detection supporting program for X-ray diagnoses. That is, the elements, such as the processing circuitry 20, for executing processing of digital information in the gesture detection supporting system 3 can be configured by a single circuit or plural circuits. For example, the elements, such as the processing circuitry 20, for executing processing of digital information in the gesture detection supporting system 3 may be at least one CPU, at least one GPU, at least one ASIC, and/or at least one PLD, such as an SPLD, a CPLD and an FPGA. Arbitrary elements for executing processing of digital information in the gesture detection supporting system 3 may also be integrated with at least one of imaging system control circuit 10 and the data processing circuit 11. Then, they read program from the memory circuitry 16 and execute the read program. That is, the gesture detection supporting program can be stored in the memory circuitry 16. The memory circuitry 16 may be integrated with the memory circuitry for storing the programs for the processing circuitry of the imaging system control system 10 and/or the data processing circuit 11.

The gesture detection supporting program is a program to function the processing circuitry 20 as a part or the whole of the gesture detection supporting system 3 for X-ray diagnoses. The gesture detection supporting program can also be recorded in an information recording medium so as to utilize a general purpose computer as at least a part of the gesture detection supporting system 3, and can be circulated as a program product. As a matter of course, the gesture detection supporting program may also be downloaded to the processing circuitry 20 via a network, without using an information recording medium.

The memory circuitry 16 also has a function to store operation contents of the X-ray diagnostic apparatus 1 respectively related to gestures of an assumed user U. Therefore, the memory circuitry 16 functions as a gesture storage part. Especially, the memory circuitry 16 can store operation contents of the X-ray diagnostic apparatus 1 corresponding to gestures according to their detection positions. Various medical instruments are placed in the examination room 2 where the X-ray diagnostic apparatus 1 is installed. Therefore, these medical instruments may become obstacles to detect gestures. Accordingly, gestures detected at positions where these obstacles can be avoided can be corresponded to operation contents of the X-ray diagnostic apparatus 1.

Figure 2:
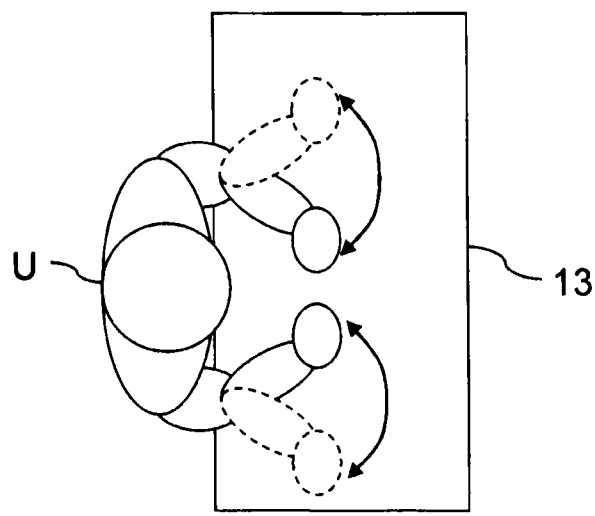
FIG. 2 is a view showing an example of gesture only by forearms.

FIG. 2 is a view showing an example of gesture only by forearms.

Gestures are generally made by motions of arms of a user U, and an arm to perform gestures can be divided from its elbow into an upper arm, which is the closer side to its shoulder, and a forearm including its hand. Accordingly, operation contents of the X-ray diagnostic apparatus 1 related to gestures only by the forearms of a user U as shown in FIG. 2 can be stored in the memory circuitry 16. Thereby, even in a case where gestures are detected from an upside of a user U, such as a ceiling 2A of the examination room 2, operations of the X-ray diagnostic apparatus 1 by gestures can be attained.

Figure 3:
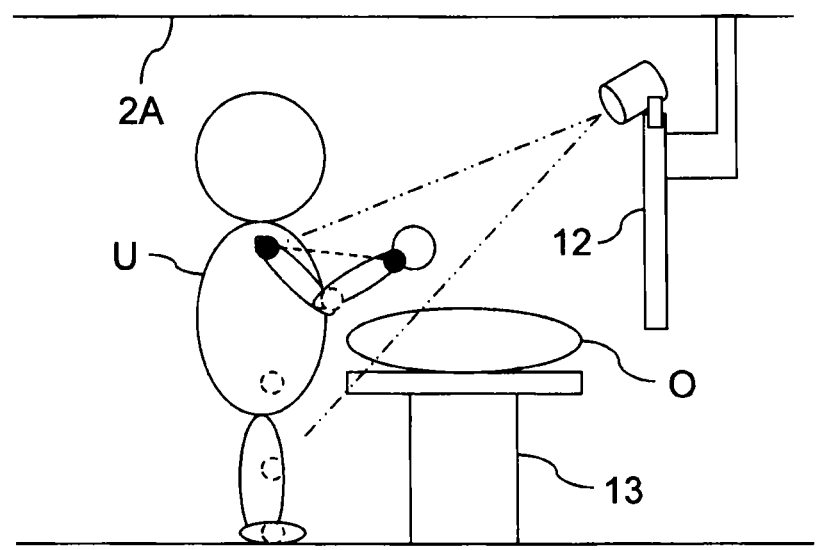
FIG. 3 is a view showing an example of gesture only by a shoulder and a wrist.

FIG. 3 is a view showing an example of gesture only by a shoulder and a wrist.

As another example, in a case that gestures are detected at a position, in an upside of a user U, looking down upon the gestures in an oblique direction, detection of elbows is difficult. Therefore, trying to detect elbows of a user U leads to detection errors of gestures and increase in loads of detection processing. Accordingly, operation contents of the X-ray diagnostic apparatus 1 related to gestures by a part including a shoulder and a wrist and excluding an elbow, as shown in FIG. 3, can be stored in the memory circuitry 16. Thereby, it becomes possible to detect gestures with excluding an elbow. Moreover, it is suitable that a position lower than the waist of a user U is not to be included in a target region of the gesture detections. By such a restriction of a detection region of gestures, gestures at a position higher than the waist of a user U can be detected effectively.

For practical examples, a method for using positions or a positional change of the two points, consisting of a wrist and a shoulder of a user U, for a gesture, or a method for using a position or a positional change of a line segment, connecting a wrist with a shoulder of a user U, for a gesture can be mentioned. In these cases, a gesture can be specified so long as at least a wrist and a shoulder of a user U are detected. Actually, a whole arm may be detected and detection data of parts excluding parts, such as a wrist and a shoulder, required for gesture detections may be removed.

Thus, gestures which are not made by a whole arm can be related to operation contents of the X-ray diagnostic apparatus 1 and can be registered in the memory circuitry 16. Thereby, even when a part of an arm cannot be detected, it is possible to operate the X-ray diagnostic apparatus 1 by gestures. However, gestures with a whole arm may surely be related to operation contents of the X-ray diagnostic apparatus 1 and can be registered in the memory circuitry 16. The operation contents of the X-ray diagnostic apparatus 1 related to gestures can be not only operation contents with regard to actions of the X-ray image acquisition system 4 but also operation contents with regard to actions of the gesture detection supporting system 3 itself.

The detecting system 17 has a function to detect a gesture of a user U and a function to give a detection result of gesture to the operation part 18. For that purpose, the detecting system 17 has at least one sensor 17A for detecting a gesture by an actual user and a detecting part 17B configured to detect a gesture based on an output from the sensor 17A. In the illustrated example, the detecting part 17B as a function of the processing circuitry 20 is included in the detecting system 17.

Therefore, the detecting system 17 is configured so that the detecting part 17B can detect a gesture of a user U based on an output from the sensor 17A. As mentioned above, gestures only by a forearm or gestures by a part including a shoulder and a wrist and excluding an elbow can be registered in the memory circuitry 16. Therefore, the detecting system 17 is configured so as to detect a gesture only by a forearm of a user U or a gesture by a part including a shoulder and a wrist and excluding an elbow of a user U, based on output from the sensor 17A.

Each sensor 17A has an attaching instrument 17C for attaching the sensors 17A to a predetermined position. It is desirable that each sensor 17A is installed at an appropriate position inside the examination room 2 where a gesture of a user U and a candidate of a user U can be detected with avoiding obstacles. Therefore, the detecting system 17 has the attaching instrument 17C for attaching the sensor 17A to a position inside the examination room 2, such as the ceiling 2A or a wall surface, higher than a predetermined height or to an instrument placed at a position higher than a predetermined height.

Moreover, each sensor 17A can have a laser irradiation function in order to indicate a detection direction. That is, each sensor 17A can have a laser light source 17D. In this case, a laser can be irradiated from the sensor 17A side toward a detection direction by manipulating a switch 17E for switching operations of the laser light source 17D. When a laser is irradiated, the laser is reflected by an obstacle placed in the detection direction, and a bright spot arises. For this reason, a user U can recognize the detection direction of the sensor 17A, and can perform gestures with awareness of the detection direction of the sensor 17A.

Furthermore, the detecting system 17 can have a movement structure 17F to move a position of the sensor 17A, a movement structure 17G to change a direction of the sensor 17A, and a control part 17H to control each of the movement structures 17F and 17G, as required. Note that, the movement structure 17F to move a position of the sensor 17A and the movement structure 17G to change a direction of the sensor 17A may be made by a common structure. The control part 17H can be installed in the detecting system 17, as a function of the processing circuitry 20 as illustrated.

In the case that the movement structures 17F and 17G are included in the detecting system 17, the relative positional relation between the sensor 17A and a user U may change. Accordingly, the control part 17H is configured to control the movement structures 17F and 17G so that at least one of a position and a direction of the sensor 17A becomes appropriate.

In addition, persons concerned, such as plural doctors and operators, exist in the examination room 2. Each of the persons concerned may alternately become a user U of the gesture detection supporting system 3. Therefore, plural candidates of a user U may be in a field of view of the sensor 17A. Accordingly, the detecting system 17 is configured to specify a user U, whose gestures should be detected, from plural candidates of a user U based on output from the sensor 17A, and to detect gestures of the specified user U based on output from the same or another sensor 17A.

In this case, the first sensor for acquiring information to specify a user U and the second sensor for detecting gestures can be individually installed in the detecting system 17. Therefore, as the sensors 17A of the detecting system 17, in addition to the first arbitrary sensor, such as a depth sensor, an optical camera or an infrared camera, according to a detection way of gestures, the second sensor, such as an optical camera or an infrared camera, is also used for recognizing the plural candidates of a user U.

However, in the case that a kind of the sensor for detecting gestures is same as a kind of the sensor for recognizing plural candidates of a user U, a same sensor may be used for detecting gestures and recognizing plural candidates of a user U. Alternatively, plural sensors may be combined and used for both of detecting gestures and detecting plural candidates of a user U. In the example shown in FIG. 1, an infrared camera is installed as the first sensor for detecting gestures while an optical camera is installed as the second sensor for specifying a user U.

On the other hand, the processing to choose a user U, as the target for detecting gestures, from plural candidates of a user U can be performed in the detecting part 17B of gestures. Conditions for specifying a user U from plural candidates of a user U can be set as suitable conditions according to a placed position of the sensor 17A and a kind of the sensor 17A.

For a specific example, in the case that a catheter can be detected by the detecting system 17, a user U judged to have held the catheter lastly can be chosen as the target for detecting gestures, based on output from the sensor 17A.

Each catheter has a shape like a wire, and even only an infrared camera can detect both a gesture and a catheter. Specifically, a catheter can be detected as a linear object by edge detection processing of infrared image data acquired by an infrared camera. Note that, a whole catheter may also be a linear marker so that the catheter can be detected easily by image processing.

However, it is preferred to place an optical camera and an infrared camera closely so as to enable to detect both a gesture and a catheter by them. In this case, the detecting part 17B can judge whether a catheter is held by a hand of a user U, by matching infrared image data acquired by the infrared camera with optical image data acquired by the optical camera. Therefore, using an optical camera can improve the detection accuracy of a catheter. Once a catheter is detected, a user U holding the catheter or a user U nearest to the catheter can be automatically judged in the detecting part 17B as the target for detecting a gesture.

As another example, a method of specifying a user U judged to be at the front of the display 12 or a user U judged to be in front of the console 9 for operating the X-ray diagnostic apparatus 1, as a user U whose gestures should be detected can be mentioned. In this case, the detecting part 17B performs processing of specifying a user U in front of the display 12 or the console 9 based on the relative positional relationship between the display 12 or the console 9 and the user U.

Moreover, processing of specifying a user U can also be performed with combining plural conditions. In this case, a user U can also be specified by not only a method for simply specifying a user U satisfying the plural conditions as the detection target of gestures but also a method for specifying a user U satisfying an exclusively chosen condition from plural conditions to which priorities have been set. Moreover, whenever one condition out of plural conditions is satisfied, the priority of the condition may be raised so that a user U corresponding to the highest priority becomes the detection target of gestures.

Thus, a gesture for specifying a user U can be omitted by such automatic judgment processing for specifying the user U. However, the specification of a user U may be performed by a gesture.

A user U specified as the target for detecting a gesture once can be tracked by the sensor 17A, with the movement structures 17F and 17G controlled by the control part 17H, so as to be always detected. Specifically, the detecting part 17B gives spatial positional information and specification information of a user U, as the detection target of gestures, to the control part 17H of the movement structures 17F and 17G. Then, the control part 17H performs feedback controls of the movement structures 17F and 17G based on the positional information of the user U so that the specified user U be in a field of view of the sensor 17A. Thereby, continuous detection of gestures by automatic tracking of the user U can be attained.

The controls of the movement structures 17F and 17G can be performed not only based on such detection information from the detecting part 17B but also based on other information.

For a specific example, a method for controlling the movement structures 17F and 17G by using a detection signal from a gyro sensor (an angular velocity sensor) as an input signal can be mentioned. When a gyro sensor is attached to the sensor 17A or the movement structures 17F and 17G, it becomes possible to recognize an angle or an angular velocity of the sensor 17A or the movement structures 17F and 17G. Accordingly, the movement structures 17F and 17G can be controlled based on a detection signal from the gyro sensor so that the sensor 17A or the movement structures 17F and 17G incline at a specific angle.

Moreover, a position and a direction of the sensor 17A can also be previously set by an operation of the input circuit 14 of the gesture detection supporting system 3. When the position and the direction of the sensor 17A are preset, it becomes possible to position the sensor 17A automatically prior to the gesture detection. As a specific example of the preset method of the position and the direction of the sensor 17A, a method for previously setting the position and the direction of the sensor 17A according to a procedure content can be mentioned. That is, a table showing positions and directions of the sensor 17A according to procedure contents can be prepared in the control part 17H.

Examples of a method for specifying a procedure content at the time of the gesture detection include a method for notifying a procedure content to the control part 17H by operation of the input circuit 14 and a method for relating a procedure content to other conditions.

As a specific example, examination protocols for controlling the X-ray diagnostic apparatus 1, kinds of application software used for X-ray diagnoses or arrangements of the imaging system 8 can be related with procedure contents. Then, the control part 17H can detect a case where an examination protocol corresponding to a procedure content has been selected, a case where an application software corresponding to a procedure content has been activated, or a case where the imaging system 8 has been arranged at a position corresponding to a procedure content, and then can control the movement structures 17F and 17G according to the detection result so that the sensor 17A is automatically positioned at the appropriate position and inclined in the appropriate direction corresponding to the procedure content. Thereby, automatic positioning of the sensor 17A corresponding to a procedure content can be attained.

Note that, the imaging system control system 10 of the X-ray diagnostic apparatus 1 can be configured to notify the control part 17H of the movement structures 17F and 17G information showing a selected examination protocol, information showing an activated application software, and/or the positional information of the imaging system 8, which is required for the processing for specifying a procedure content in the control part 17H.

The position of the sensor 17A can be also adjusted by manual control of the movement structures 17F and 17G besides automatic control or semiautomatic control of the movement structures 17F and 17G as mentioned above. In a case of adjusting the position of the sensor 17A manually, the movement structures 17F and 17G can be controlled by operation of the input circuit 14 or a gesture. In a case of controlling the movement structures 17F and 17G by a gesture, what is necessary is to relate gestures with drive contents of the movement structures 17F and 17G in advance and to register the related gestures in the memory circuitry 16. In this case, the control part 17H is to control the movement structures 17F and 17G according to a drive content of the movement structures 17F and 17G corresponding to a gesture detected by the detecting part 17B. On the other hand, it is possible to control the movement structures 17F and 17G manually by directing a drive content of the movement structures 17F and 17G from the input circuit 14 to the control part 17H. Thereby, manual operation of the sensor 17A can be attained.

Next, examples of arrangement of the sensor 17A, and functions and configurations of the detecting system 17 according to a position of the sensor 17A will be described. Note that, examples of arranging a single sensor 17A will be shown below. In a case that the second sensor for specifying a user U is installed in addition to the first sensor for detecting a gesture, the second sensor can be installed at a position similar to a position of the first sensor or another suitable position, according to a specification method of a user U.

Figure 4:
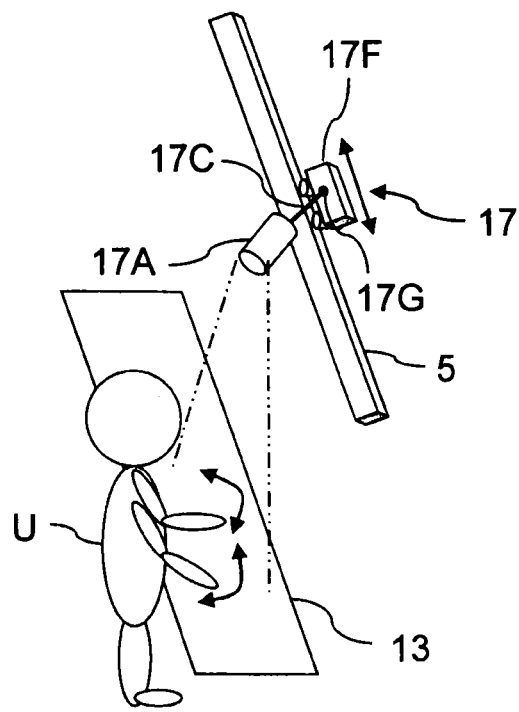
FIG. 4 is a view showing the first example of position for attaching the sensor shown in FIG. 1.

FIG. 4 is a view showing the first example of position for attaching the sensor 17A shown in FIG. 1.

As shown in FIG. 4, the sensor 17A can be installed so that the sensor 17A can move along the arm 5 for driving the X-ray tube 6 and the X-ray detector 7 of the X-ray diagnostic apparatus 1. In this case, the attaching instrument 17C for attaching the sensor 17A to the arm 5 is provided with the sensor 17A. Moreover, the movement structures 17F and 17G for moving the sensor 17A along the arm 5 for driving the imaging system 8 of the X-ray diagnostic apparatus 1 are installed on the arm 5. The structures of the attaching instrument 17C and the movement structures 17F and 17G are arbitrary. For example, the sensor 17A can be attached to the movement structures 17F and 17G, which move along a C-shaped arm as a rail, with the attaching instrument 17C, such as a fixing bracket.

In this case, the sensor 17A moves along the rail. Therefore, the sensor 17A can be placed at a position where a user U can be looked down. Moreover, there is no instruments which may be obstacles between the sensor 17A and a user U, and simultaneously, the position of the sensor 17A can be easily adjusted along the rail. Therefore, a user U can be certainly in a field of view of the sensor 17A.

Furthermore, the sensor 17A can certainly detect at least a forearm part of a user U. Therefore, registering gestures by moving a forearm part to right and left in the memory circuitry 16 can prevent a detection error of gesture. Moreover, a burdensome gesture disturbing a procedure, such as a gesture which a user U performs with raising an arm, can be avoided.

Figure 5:
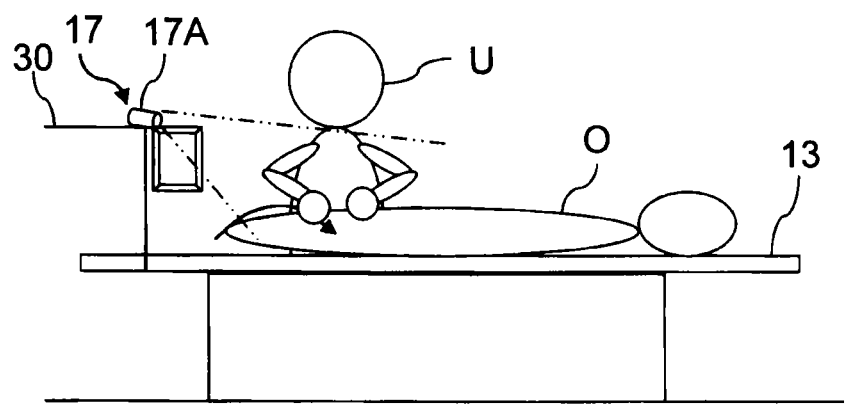
FIG. 5 is a view showing the second example of position for attaching the sensor shown in FIG. 1.

FIG. 5 is a view showing the second example of position for attaching the sensor 17A shown in FIG. 1.

As shown in FIG. 5, the sensor 17A can also be installed on an intravenous drip stand 30. In this case, the attaching instrument 17C, such as a fixing bracket, for attaching the sensor 17A to the intravenous drip stand 30 is provided with the sensor 17A. Note that, the sensor 17A may be attached with an instrument placed near a user U, such as an injector of a contrast agent, as well as the intravenous drip stand 30. In this case, a gesture of a user U can be detected favorably since the position of the sensor 17A becomes near the user U and there is no instruments which may be obstacles between the sensor 17A and a user U.

Figure 6:
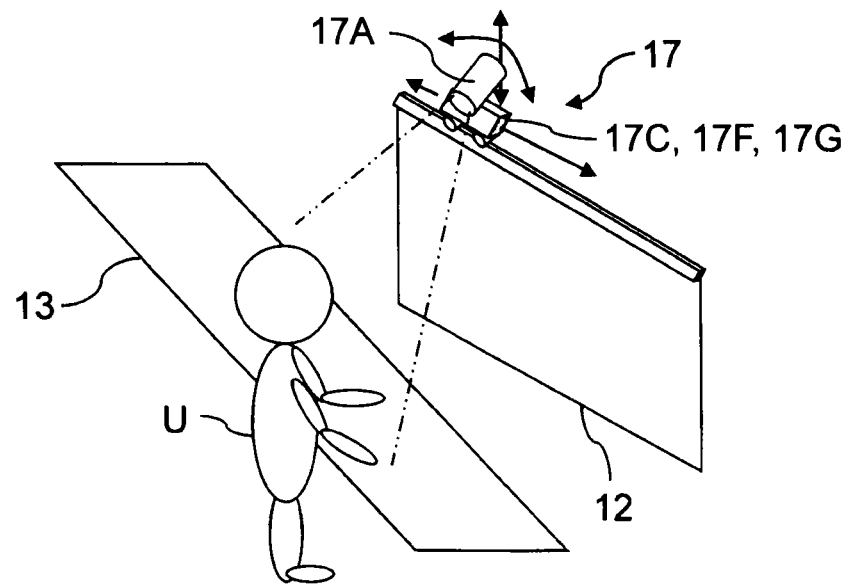
FIG. 6 is a view showing the third example of position for attaching the sensor shown in FIG. 1.

FIG. 6 is a view showing the third example of position for attaching the sensor 17A shown in FIG. 1.

As shown in FIG. 6, the sensor 17A can also be installed so that the sensor 17A can move along an edge of the display 12, such as an FPD (flat panel display), for displaying X-ray image data acquired by the X-ray diagnostic apparatus 1. In this case, the attaching instrument 17C for attaching the sensor 17A to the display 12 is provided with the sensor 17A. Moreover, the movement structures 17F and 17G for moving the sensor 17A along the edge of the display 12 are installed. The structures of the attaching instrument 17C and the movement structures 17F and 17G are arbitrary. For example, the sensor 17A can be attached to the movement structures 17F and 17G, functioning as the attaching instrument 17C which moves along the edge of the display 12 as a rail, with a fixing bracket or the like, as illustrated.

The display 12 is usually placed near a lateral side of a user U. Therefore, there is no obstacles between the display 12 and the sensor 17A. Besides, the position of the sensor 17A can be moved in parallel along the edge of the display 12 by drive of the movement structures 17F and 17G. For this reason, a gesture of a user U can be detected from a suitable position without obstacles.

Note that, in a case of the display 12 having a large screen, such as a monitor for X-ray live images, a monitor stand itself on which the display 12 is installed may be movable. Accordingly, the position of the sensor 17A may be adjusted according to the position of the display 12.

Furthermore, a function to swing the sensor 17A can also be provided by the movement structure 17G so as to be able to change the direction of the sensor 17A. In this case, the sensor 17A can rotate in addition to move in parallel. For this reason, a user U can always be kept in a field of view of the sensor 17A by adjusting the position and the direction of the sensor 17A.

Note that, the movement structure 17G having the swing function of the sensor 17A can be installed to various objects including not only the display 12 but the arm 5. The control part 17H performs controls of the movement structures 17F and 17G for adjusting the position and the direction of the sensor 17A. The controls of the movement structures 17F and 17G can be performed according to arbitrary algorithms. Moreover, the control part 17H may control the movement structures 17F and 17G referring to a processing result of the detecting part 17B.

For example, the detecting part 17B can detect a still or moving user U from image data acquired using the sensor 17A, such as an optical camera, by arbitrary image processing, such as marker detection or edge detection, as mentioned above. Then, the control part 17H can control the movement structures 17F and 17G so that the detected user U can be tracked by the sensor 17A.

Alternatively, in a case where an instrument, such as the arm 5 or a large screen monitor, to be an attaching target of the sensor 17A and the movement structures 17F and 17G moves, the control part 17H can be configured to acquire positional information of the instrument with which the sensor 17A and the movement structures 17F and 17G are attached. Then, the control part 17H can control the movement structures 17F and 17G so that a movement distance of the instrument with which the sensor 17A and the movement structures 17F and 17G are attached is canceled. Thereby, the position of the sensor 17A can be kept constant even when the instrument with which the sensor 17A is attached moves. Note that, examples of a possibly moving instrument, with which the sensor 17A is attached, include the arm 5 for moving the imaging system 8 and a large screen monitor for live images, as mentioned above.

Besides, the control part 17H can also control the movement structures 17F and 17G so that the position and direction of the sensor 17A become a preset position and direction according to a procedure content as mentioned above. The control conditions of the movement structures 17F and 17G by the control part 17H may also be determined alternatively from plural conditions, as mentioned above. Alternatively, the control conditions of the movement structures 17F and 17G may also be determined with combining plural conditions and setting priority orders thereof, as mentioned above.

Therefore, the control part 17H can be configured to control the movement structures 17F and 17G so that at least one of the position and the and direction of the sensor 17A becomes appropriate according to at least one of a position of the sensor 17A, a position of a user U, a position of the arm 5, a position of the display 12, and a procedure content in X-ray diagnosis. Especially, the control part 17H can also be configured to control the movement structures 17F and 17G so that a gesture of a user U selected from plural users U based on the relative position to the arm 5 or the display 12 can be detected.

Figure 7:
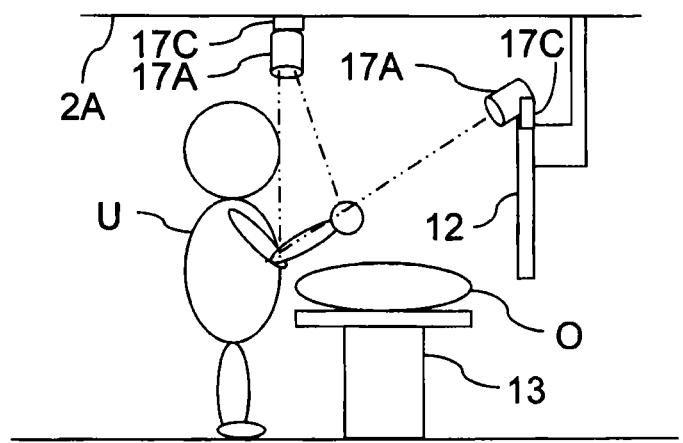
FIG. 7 is a view showing the fourth example of position for attaching the sensor shown in FIG. 1.

FIG. 7 is a view showing the fourth example of position for attaching the sensor 17A shown in FIG. 1.

As shown in FIG. 7, the sensor 17A may also be attached to the ceiling 2A of the examination room 2 where the X-ray diagnostic apparatus 1 is placed. In this case, the attaching instrument 17C, such as a fixing bracket, for attaching the sensor 17A to the ceiling 2A of the examination room 2 is provided with the sensor 17A. As a matter of course, the sensor 17A may be moved by the movement structures 17F and 17G with a rail fixed on the ceiling 2A.

When the sensor 17A is attached to the ceiling 2A, it becomes possible to detect a gesture from right above of a user U as shown in FIG. 2. For this reason, a gesture only by a forearm can be suitably detected with avoiding obstacles. Therefore, raising an arm by a user U can be avoided. Especially, in the case that the sensor 17A is installed on the ceiling 2A, the sensor 17A faces the forearm part of a user U. Therefore, the detection accuracy of a motion of a forearm part can be improved compared with a case that the sensor 17A is installed at a position, such as the display 12, from which a user U is looked down on in an oblique direction.

In addition, the sensor 17A may also be installed on the display 12 as shown in FIG. 7 so that the sensor 17A on the display 12 side can detect a gesture by a part including a shoulder and a wrist and excluding an elbow. This will enable to improve the detection accuracy of a gesture wherever a user U stands.

Besides the above-mentioned examples, the sensor 17A may be attached to various places inside the examination room 2. For example, the sensor 17A may be attached to an X-ray protective board near a user U, which can avoid obstacles.

Next, functions of other elements of the gesture detection supporting system 3 will be described.

The operation part 18 has a function to output operation information to the X-ray diagnostic apparatus 1, based on a detection result of a gesture by the detecting system 17. More specifically, the operation part 18 is configured to acquire a corresponding operation content of the X-ray diagnostic apparatus 1, from the memory circuitry 16, based on a detection result of a gesture, and to output operation information to the X-ray diagnostic apparatus 1, based on the acquired operation content.

Moreover, gestures may be related with control contents of the movement structures 17F and 17G of the sensor 17A. In this case, the operation part 18 is configured to acquire an operation content of a corresponding movement structure 17F or 17G, from the memory circuitry 16, based on a detection result of a gesture, and to output control information to the control part 17H of the movement structures 17F and 17G, based on the acquired operation content.

The control part 19 has a function to control each element of the gesture detection supporting system 3. For example, when a condition under which a gesture should not be detected has been detected, the control part 19 is configured to stop processing of at least one of the detecting system 17 and the operation part 18. Thereby, a detection error of a gesture can be prevented.

A case where a user U is performing a procedure is a typical case where a gesture should not be detected. Accordingly, arbitrary conditions each indicating that a procedure is being performed can be each defined as a case where a gesture should not be detected.

As a specific example, when a user U is operating a catheter, it can be judged to be under a procedure. On the other hand, when a user U intends to operate the X-ray diagnostic apparatus 1 by a gesture, the hands of the user U get away from a catheter. Accordingly, a catheter can be detected using a depth sensor or an optical camera as the sensor 17A, as mentioned above. Then, the case that the catheter is not away from the hands can be defined as a condition under which a gesture should not be detected, i.e., a stopping condition of an operation by a gesture.

Figure 8:
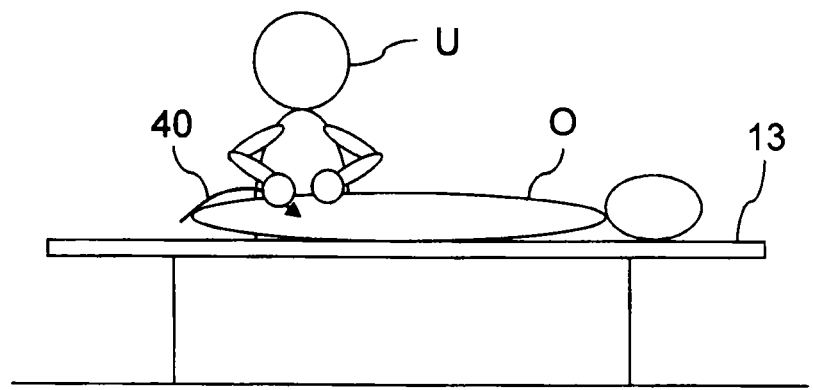
FIG. 8 is a view showing an example of switching the operation function by gestures according to whether a hand of a user is away from a catheter.
Figure 8:
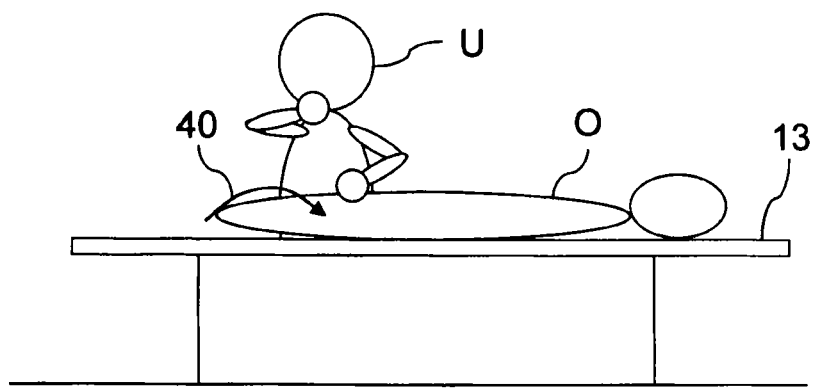

FIG. 8 is a view showing an example of switching the operation function by gestures according to whether a hand of a user U is away from a catheter.

FIG. 8 (A) shows a state where a user U is operating a catheter 40 by a hand and FIG. 8 (B) shows a state where the hands of a user U are away from the catheter 40. As shown in FIG. 8 (A), when a hand of a user U is judged to contact with the catheter 40, the operation function by a gesture can be turned to the OFF state. On the contrary, as shown in FIG. 8 (B), when hands of a user U are judged not to contact with the catheter 40, the operation function by a gesture can be turned to the ON state.

By the control as mentioned above, detection of gestures or operation of the X-ray diagnostic apparatus 1 based on a detected gesture can be performed only in the case that the hands of a user U are away from the catheter 40. As a result, an incorrect detection of a gesture can be avoided.

As another example, while a user U is operating the catheter 40, the wrists of the user U are not raised too higher than the elbows. Accordingly, the wrists and the elbows of a user U can be detected by the sensor 17A. Then, a case that the a position of a wrist has become higher than that of the elbow by not less than a predetermined distance can be defined as a condition under which a gesture should not be detected, i.e., a stopping condition of an operation by a gesture.

Figure 9:
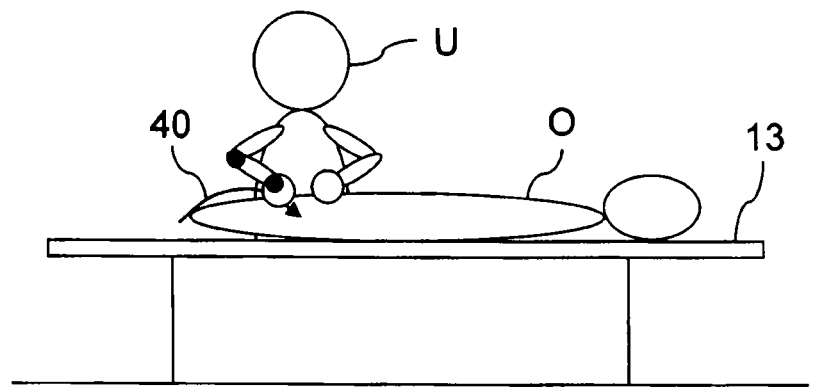
FIG. 9 is a view showing an example of switching the operation function by gestures based on the relation between heights of a wrist and an elbow of a user.
Figure 9:
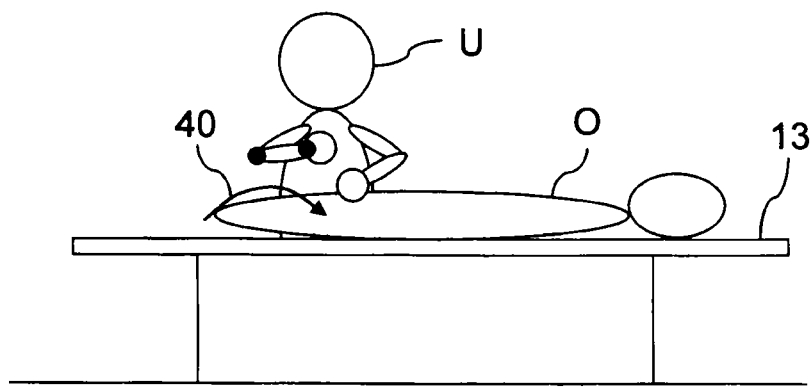

FIG. 9 is a view showing an example of switching the operation function by gestures based on the relation between heights of a wrist and an elbow of a user U.

As shown in FIG. 9 (A), while a user U is operating the catheter 40, the wrists of the user U are generally lower than the elbows. For this reason, when the positions of the wrists are not higher than those of the elbows by not less than a predetermined distance in consideration of an individual variation of a user U, the operation function by a gesture can be turned to the OFF state. On the contrary, as shown in FIG. 9 (B), when a position of a wrist of a user U has become higher than that of the elbow by not less than the predetermined distance, the operation function by a gesture can be switched to the ON state.

The conditions shown in FIG. 8 and FIG. 9 can also be combined and set. Therefore, at least one of the catheter 40 and relative positional relations between the wrists and the elbows of a user U can be detected based on output from the sensor 17A for the gesture detection or another sensor 17A. Then, in the case that the relative positional relations between the wrists and the elbows have become predetermined conditions or in the case that the catheter 40 is judged to be held by a hand of a user U, processing of at least one of the detecting system 17 and the operation part 18 can be stopped. For that purpose, the control part 19 is configured to acquire detection data, required for judging the stop conditions of operations by gestures, from the detecting part 17B of the detecting system 17, and to judge whether the stop conditions of operations by gestures are satisfied or not, based on the acquired detection data.

In addition to the above-mentioned features, at least one of the detecting system 17 and the operation part 18 can be configured to perform processing with targeting a range higher than a predetermined height. As a specific example, the detection of a gesture or the processing of specifying operation information based on a detected gesture can be performed with targeting a range higher than a height set to correspond to the waist of a user U.

When the sensor 17A is arranged above a user U as mentioned above, the bed 13 or the like may become an obstacle, and consequently, a part lower than the waist of a user U may be outside a field of view of the sensor 17A. Accordingly, the gesture detection or the processing of specifying operation information based on a detected gesture may not be performed in a range lower than a height corresponding to the waist of a user U. Thereby, an incorrect detection of a gesture, ineffectual data processing, and a runaway of the processing circuitry 20 can be avoided.

Next, operations and actions of the gesture detection supporting system 3 and the X-ray diagnostic apparatus 1 will be described.

Figure 10:
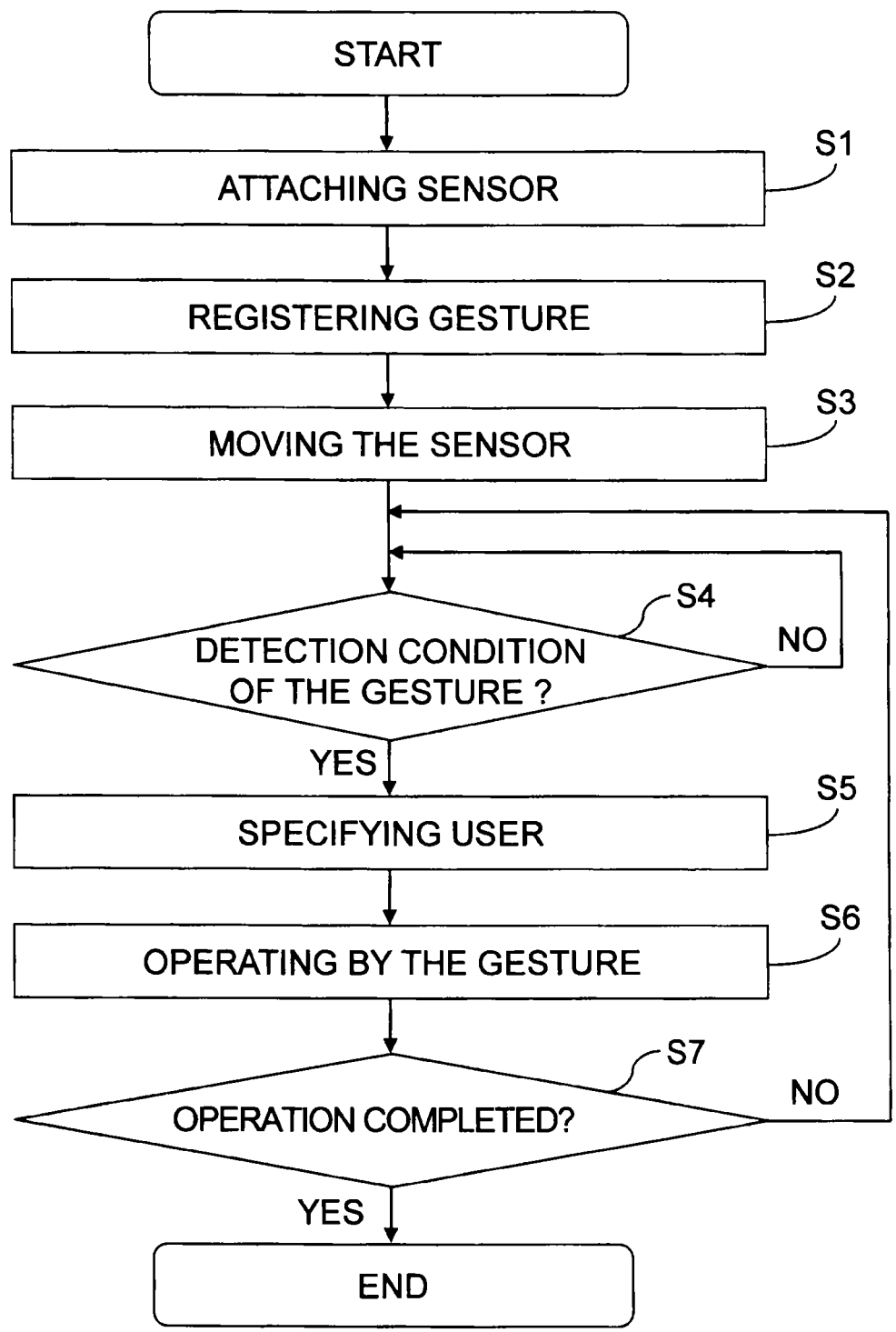
FIG. 10 is a flow chart which shows an example flow of an X-ray diagnosis with operations by gestures using the gesture detection supporting system and the X-ray diagnostic apparatus shown in FIG. 1.

FIG. 10 is a flow chart which shows an example flow of an X-ray diagnosis with operations by gestures using the gesture detection supporting system 3 and the X-ray diagnostic apparatus 1 shown in FIG. 1.

At first, in Step S1, the sensor 17A of the gesture detection supporting system 3 is attached to a position, suitable for the gesture detection, inside the examination room 2. For a specific example, a single or plural sensors 17A are attached to arbitrary positions, such as the arm 5 of the X-ray diagnostic apparatus 1, the intravenous drip stand 30, the display 12, and/or the ceiling 2A, with the attaching instruments 17C as illustrated from FIG. 4 to FIG. 7. A single or plural sensors 17A may be attached with an injector of a contrast agent and/or an X-ray protective board.

Next, in Step S2, gestures according to the positions where the sensors 17A have been attached are related with operation contents of the X-ray diagnostic apparatus 1 and registered in the memory circuitry 16 of the gesture detection supporting system 3. For that purpose, the processing circuitry 20 of the gesture detection supporting system 3 reads the gesture detection supporting program from the memory circuitry 16 and executes the gesture detection supporting program. Especially, gestures, such as gestures only by a forearm and/or gestures by a part including a shoulder and a wrist and excluding an elbow, can be registered in consideration of a circumstance having many obstacles inside the examination room 2 for X-ray diagnoses.

Next, in Step S3, when the movement structures 17F and 17G of the sensors 17A have been installed, the positions of the sensors 17A are moved to the initial positions. For example, the sensors 17A can be positioned to preset positions corresponding to a procedure content. Subsequently, the control part 17H controls the movement structures 17F and 17G so as to adapt at least one of a position or a direction of sensors 17A with at least one of positions of sensors 17A, a position of the actual user U, a position of the arm 5, a position of the display 12 and a procedure content in the X-ray diagnosis, for example.

Next, in Step S4, the control part 19 of the gesture detection supporting system 3 judges whether detection conditions of a gesture have been satisfied. Specifically, the control part 19 refers to information, such as a positional relation between a wrist and an elbow of a user U and/or a positional relation between the catheter 40 and a wrist, which indirectly indicates whether it is under a procedure or not, based on an output from the sensor 17A, such as an optical camera.

When it is judged that the detection conditions of a gesture have not been satisfied, the control part 19 switches the operation of at least one of the detecting system 17 and the operation part 18 into the OFF state. For this reason, the gesture detection supporting system 3 becomes in a standby state until it is judged that the detection conditions of a gesture have been satisfied.

On the other hand, when it is judged that the detection conditions of a gesture have been satisfied, the detecting system 17 performs processing for specifying a detection target of a gesture, from plural candidates of a user U, in Step S5. Specifically, a user U judged to have held a catheter 40 lastly or a user U judged to be in front of the display 12 or the console 9 is specified as a user U, whose gesture should be detected, by the detecting part 17B based on an output from the sensor 17A, such as an optical camera or an infrared camera.

Note that, the processing in Step S5 for specifying a user U may be performed prior to the processing in Step S4 for judging whether the detection conditions of a gesture have been satisfied or not.

Next, in Step S6, a gesture detection and an operation of the X-ray diagnostic apparatus 1 based on a detected gesture are performed. Specifically, when a user U performs a gesture, image data of the gesture acquired by the sensors 17A are output to the detecting part 17B. Then, the detecting part 17B detects the gesture by known processing of the image data.

Figure 11:
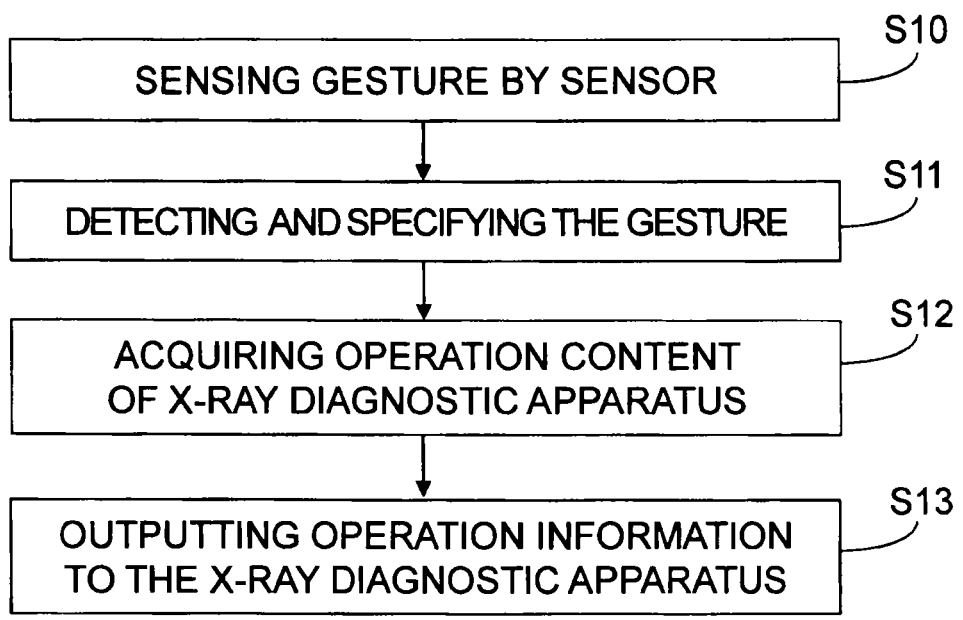
FIG. 11 is a flowchart showing a detail of Step 6 of the flowchart shown in FIG. 10.

FIG. 11 is a flowchart showing a detail of Step 6 of the flowchart shown in FIG. 10.

In Step S10, at least one sensor 17A senses a gesture by an actual user U. Next, in Step S11, the detecting part 17B detects and specifies the gesture by the actual user, based on an output from the at least sensor 17A. For example, the detecting part 17B can detect and specify a gesture by only a forearm of the actual user or a gesture by a part, including a shoulder and a wrist and excluding an elbow, of the actual user.

In this case, tracking of a user U is performed by drives of the movement structures 17F and 17G, as needed, such as in a case where the user U has moved. When a user U is tracked, image data of the user U acquired by the sensor 17A are given to the control part 17H through the detecting part 17B. Then, the control part 17H controls the movement structures 17F and 17G of the sensors 17A so that the user U should be in fields of view of the sensors 17A. For example, the control part 17H controls the movement structures 17F and 17G so as to enable the sensors 17A to detect a gesture by the actual user selected from candidates based on a relative position between the selected actual user and the arm 5 or the display 12.

Next, the detected gesture is given to the operation part 18. Then, in Step S12, the operation part 18 acquires an operation content of the X-ray diagnostic apparatus 1 corresponding to the gesture from the memory circuitry 16, based on a detection result of the gesture by the actual user. Subsequently, in Step S13, the operation part 18 outputs operation information to the X-ray diagnostic apparatus 1, based on the acquired operation content. In this case, the operation part 18 may output the operation information to the X-ray diagnostic apparatus when the gesture by the actual user has been detected from a range higher than a predetermined height.

Consequently, the X-ray diagnostic apparatus 1 drives according to the operation information. For example, when the operation information directs the start of the X-ray imaging, the X-ray image acquisition system 4 starts X-ray imaging. Meanwhile, when the operation information directs a drive of the imaging system 8, the imaging system 8 is positioned to a predetermined position according to the drive direction.

Next, in Step S7, the control part 19 judges whether operations of the X-ray diagnostic apparatus 1 by gestures have been completed or not. For example, in the case that a direction of completing the gesture operation has been input from the input circuit 14 into the control part 19, or in the case that a direction of completing the operation has been input from the console 9 into the X-ray diagnostic apparatus 1 and the direction of completing the operation has given from the imaging system control system 10 of the X-ray diagnostic apparatus 1 to the control part 19, the control part 19 judges that operations by gestures have been completed. In this case, the operation of the gesture detection supporting system 3 terminate.

On the other hand, when the control part 19 judges that operations by gestures have not been completed, the control part 19 judges whether the detection conditions of a gesture part 19 have been satisfied or not in Step S4 again.

For example, the detecting part 17B can detects at least one of a relative position relationship between a wrist and an elbow of the actual user U and a catheter, based on another output from the sensor 17A for detecting gestures or another sensor 17A. When the relative position relationship between the wrist and the elbow has become a predetermined condition or when the catheter is determined to be held with a hand of the actual user U, the processing circuitry 20 can stop at least one of detecting a following gesture by the actual user U and outputting following operation information.

Thus, by repeating an operation of the X-ray diagnostic apparatus 1 by a gesture, a procedure, such as TAVR (Trans-catheter Aortic Valve Implantation) or TAVI (Trans-catheter Aortic Valve Replacement), can be performed with referring to X-ray images.

That is, the gesture detection supporting system 3 and the X-ray diagnostic apparatus 1 mentioned above are configured to be operated by detecting a gesture of a user U effectively inside the examination room 2 where various medical equipments and instruments are installed.

For this reason, the gesture detection supporting system 3 and the X-ray diagnostic apparatus 1 can have the operation function by gesture work effectively and can reduce operation labor by a user U. For a specific example, the sensors 17A for detecting gestures can be attached to suitable positions. Further, gestures according to positions where the sensors 17A are attached can be registered. For this reason, the X-ray diagnostic apparatus 1 can be operated by a gesture within a usual action range for a procedure or the like. Moreover, even when a part of an arm of a user U cannot be detected by the sensor 17A, it are possible to detect a gesture and to operate the X-ray diagnostic apparatus 1.

Moreover, fields of view of the sensors 17A can be adjusted to a position of a user U by installing the movement structures 17F and 17G of the sensors 17A. In addition, in the case where plural candidates of a user U have been detected, a user U whose gesture should be detected can be detected automatically and can also track the detected user U. For this reason, a gesture for recognizing a user U can be omitted.

Furthermore, in a case where an operation of the X-ray diagnostic apparatus 1 by a gesture is not presumed although an arm of a user U are moving, such as a case that a user U is holding the catheter 40, the detection of a gesture can be switched to the OFF state automatically. For this reason, an improper operation of the X-ray diagnostic apparatus 1 by a gesture is avoidable.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A gesture detection supporting system for an X-ray diagnosis comprising:
at least one sensor configured to sense a gesture by an actual user and a catheter, the gesture and the catheter being sensed by an image processing of at least one image acquired by at least one camera;
memory circuitry configured to store an operation content of an X-ray diagnostic apparatus, the operation content being related to a gesture by an assumed user; and
processing circuitry configured to
detect the gesture by the actual user, based on an output from the at least one sensor,
acquire the operation content of the X-ray diagnostic apparatus, from said memory circuitry, based on a detecting result of the gesture by the actual user,
output operation information to the X-ray diagnostic apparatus, based on the acquired operation content,
detect the catheter, based on another output from the at least one sensor or another sensor, and
stop at least one of detecting a following gesture by the actual user and outputting following operation information when the catheter is determined to be held with a hand of the actual user.

2. A gesture detection supporting system for an X-ray diagnosis comprising:
at least one sensor configured to sense candidates of an actual user, the candidates being sensed by image processing of an image acquired by a camera;
memory circuitry configured to store an operation content of an X-ray diagnostic apparatus, the operation content being related to a gesture by an assumed user; and
processing circuitry configured to
specify an actual user from the candidates, based on an output from the at least one sensor,
detect a gesture by the specified actual user, based on another output from the at least one sensor or another sensor,
acquire the operation content of the X-ray diagnostic apparatus, from said memory circuitry, based on a detection result of the gesture by the actual user, and
output operation information to the X-ray diagnostic apparatus, based on the acquired operation content,
wherein said processing circuitry is configured to specify the actual user as a user who is determined to have held a catheter last, a user who is determined to be in front of a display for displaying an X-ray image acquired by the X-ray diagnostic apparatus, or a user who is determined to be in front of a console for operating the X-ray diagnostic apparatus.

3. The gesture detection supporting system for an X-ray diagnosis of claim 1, wherein said processing circuitry is configured to detect a gesture by only a forearm of the actual user or a gesture by a part, including a shoulder and a wrist and excluding an elbow, of the actual user.

4. The gesture detection supporting system for an X-ray diagnosis of claim 1, wherein said processing circuitry is configured to specify the actual user from candidates, based on another output from the at least one sensor or another sensor.

5. The gesture detection supporting system for an X-ray diagnosis of claim 1, wherein said processing circuitry is configured to output the operation information to the X-ray diagnostic apparatus when the gesture by the actual user has been detected from a range higher than a predetermined height.

6. The gesture detection supporting system for an X-ray diagnosis of claim 2, wherein said processing circuitry is configured to detect a gesture by only a forearm of the actual user or a gesture by a part, including a shoulder and a wrist and excluding an elbow, of the actual user.

7. The gesture detection supporting system for an X-ray diagnosis of claim 2, wherein said processing circuitry is configured to output the operation information to the X-ray diagnostic apparatus when the gesture by the actual user has been detected from a range higher than a predetermined height.

8. An X-ray diagnostic system comprising:
an X-ray diagnostic apparatus;
at least one camera;
at least one sensor configured to sense a gesture by an actual user and a catheter, the gesture and the catheter being sensed by an image processing of at least one image acquired by the at least one camera;
memory circuitry configured to store an operation content of the X-ray diagnostic apparatus, the operation content being related to a gesture by an assumed user; and
processing circuitry configured to
detect the gesture by the actual user, based on an output from the at least one sensor,
acquire the operation content of the X-ray diagnostic apparatus, from said memory circuitry, based on a detecting result of the gesture by the actual user,
output operation information to the X-ray diagnostic apparatus, based on the acquired operation content,
detect the catheter, based on another output from the at least one sensor or another sensor, and
stop at least one of detecting a following gesture by the actual user and outputting following operation information when the catheter is determined to be held with a hand of the actual user.

9. An X-ray diagnostic system comprising:
an X-ray diagnostic apparatus;
a camera;
at least one sensor configured to sense candidates of an actual user, the candidates being sensed by image processing of an image acquired by the camera;
memory circuitry configured to store an operation content of the X-ray diagnostic apparatus, the operation content being related to a gesture by an assumed user; and
processing circuitry configured to
specify an actual user from the candidates, based on an output from the at least one sensor,
detect a gesture by the specified actual user, based on another output from the at least one sensor or another sensor,
acquire the operation content of the X-ray diagnostic apparatus, from said memory circuitry, based on a detection result of the gesture by the actual user, and
output operation information to the X-ray diagnostic apparatus, based on the acquired operation content,
wherein said processing circuitry is configured to specify the actual user as a user who is determined to have held a catheter last, a user who is determined to be in front of a display for displaying an X-ray image acquired by the X-ray diagnostic apparatus, or a user who is determined to be in front of a console for operating the X-ray diagnostic apparatus.

10. A gesture detection method for an X-ray diagnosis comprising:
sensing, using at least one sensor, a gesture by an actual user and a catheter, the gesture and the catheter being sensed by an image processing of at least one image acquired by at least one camera;

storing in memory circuitry an operation content of an X-ray diagnostic apparatus, the operation content being related to a gesture by an assumed user;

detecting the gesture by the actual user, based on an output from the at least one sensor;

acquiring the operation content of the X-ray diagnostic apparatus, from said memory circuitry, based on a detecting result of the gesture by the actual user;

outputting operation information to the X-ray diagnostic apparatus, based on the acquired operation content;

detecting the catheter, based on another output from the at least one sensor or another sensor; and stopping at least one of detecting a following gesture by the actual user and outputting following operation information when the catheter is determined to be held with a hand of the actual user.

11. A gesture detection method for an X-ray diagnosis comprising:

sensing, using at least one sensor, candidates of an actual user, the candidates being sensed by image processing of an image acquired by a camera;

storing in memory circuitry an operation content of an X-ray diagnostic apparatus, the operation content being related to a gesture by an assumed user;

specifying an actual user from the candidates, based on an output from the at least one sensor, detecting a gesture by the specified actual user, based on another output from the at least one sensor or another sensor, acquiring the operation content of the X-ray diagnostic apparatus, from said memory circuitry, based on a detection result of the gesture by the actual user, and outputting operation information to the X-ray diagnostic apparatus, based on the acquired operation content, wherein said processing circuitry is configured to specify the actual user as a user who is determined to have held a catheter last, a user who is determined to be in front of a display for displaying an X-ray image acquired by the X-ray diagnostic apparatus, or a user who is determined to be in front of a console for operating the X-ray diagnostic apparatus.

\* \* \* \* \*